United States Patent [19]
Fitch et al.

[11] Patent Number: 5,563,337
[45] Date of Patent: Oct. 8, 1996

[54] MOISTURE MONITOR APPARATUS FOR A FLUID SYSTEM

[75] Inventors: James C. Fitch; Simeon Jaggernauth, both of Tulsa, Okla.; Kym Bergstrom, Wichita Falls, Tex.

[73] Assignee: Diagnetics, Inc., Tulsa, Okla.

[21] Appl. No.: 322,057

[22] Filed: Oct. 12, 1994

[51] Int. Cl.⁶ .................................................. G01N 33/20
[52] U.S. Cl. ........................ 73/61.430; 73/61.46
[58] Field of Search ................. 73/61.43, 61.46, 73/61.76, 61.77

[56] References Cited

U.S. PATENT DOCUMENTS

| | | | |
|---|---|---|---|
| 4,116,045 | 9/1978 | Potter | 73/61.1 R |
| 4,159,638 | 7/1979 | Potter | 73/61.1 R |
| 4,202,203 | 5/1980 | Potter | 73/61.1 R |
| 4,251,809 | 2/1981 | Cheney | 340/603 |
| 4,589,277 | 5/1986 | Collins et al. | 73/61.1 R |
| 5,380,091 | 1/1995 | Buchanan | 73/61.3 |
| 5,433,105 | 7/1995 | Takahashi et al. | 73/61.46 |

FOREIGN PATENT DOCUMENTS

| | | | |
|---|---|---|---|
| 208096 | 1/1987 | European Pat. Off. | |
| 91305358 | 6/1991 | European Pat. Off. | G01F 1/74 |
| 57-0105437 | 6/1982 | Japan | G01N 25/58 |
| 57-0204467 | 11/1982 | Japan | G01N 25/56 |
| 58-223049 | 12/1983 | Japan | |

*Primary Examiner*—Thomas P. Noland
*Assistant Examiner*—Jay L. Politzer
*Attorney, Agent, or Firm*—Head, Johnson & Kachigian

[57] ABSTRACT

A moisture monitor apparatus for a fluid system. The apparatus includes a heater in fluid communication with the fluid system to heat the fluid in the fluid system. A microphone transmits sounds produced as the moisture vaporizes from heating and converts the sounds into electric voltage variations. The electric voltage variations are translated into quantitative data to determine the level of moisture in the fluid.

12 Claims, 3 Drawing Sheets

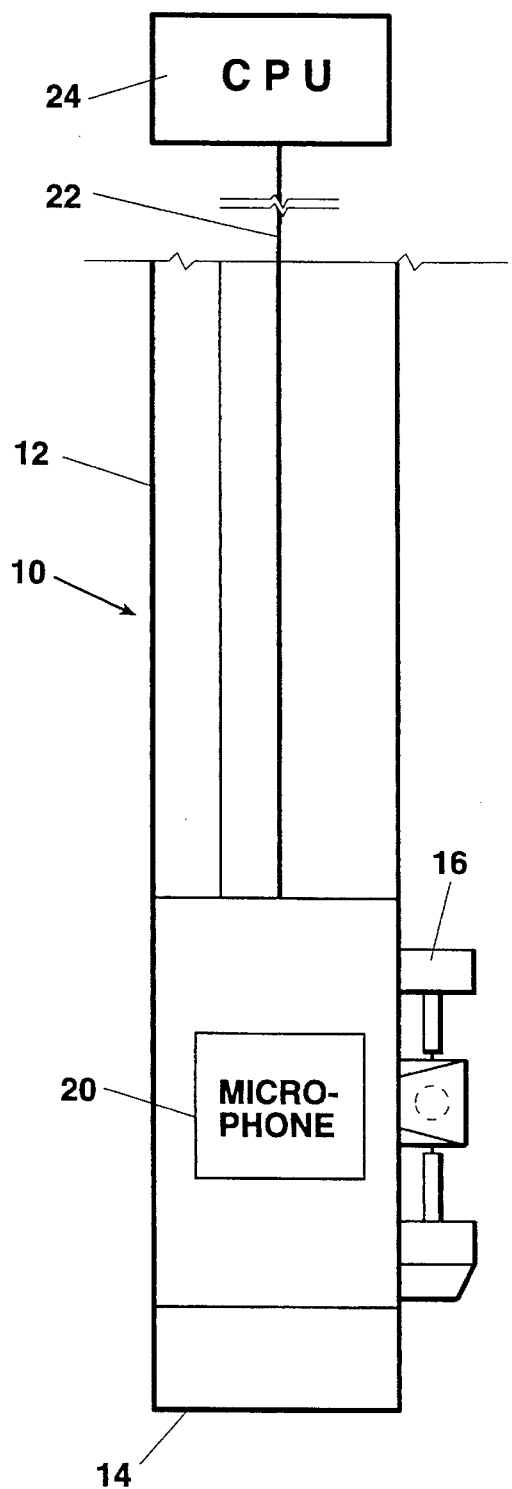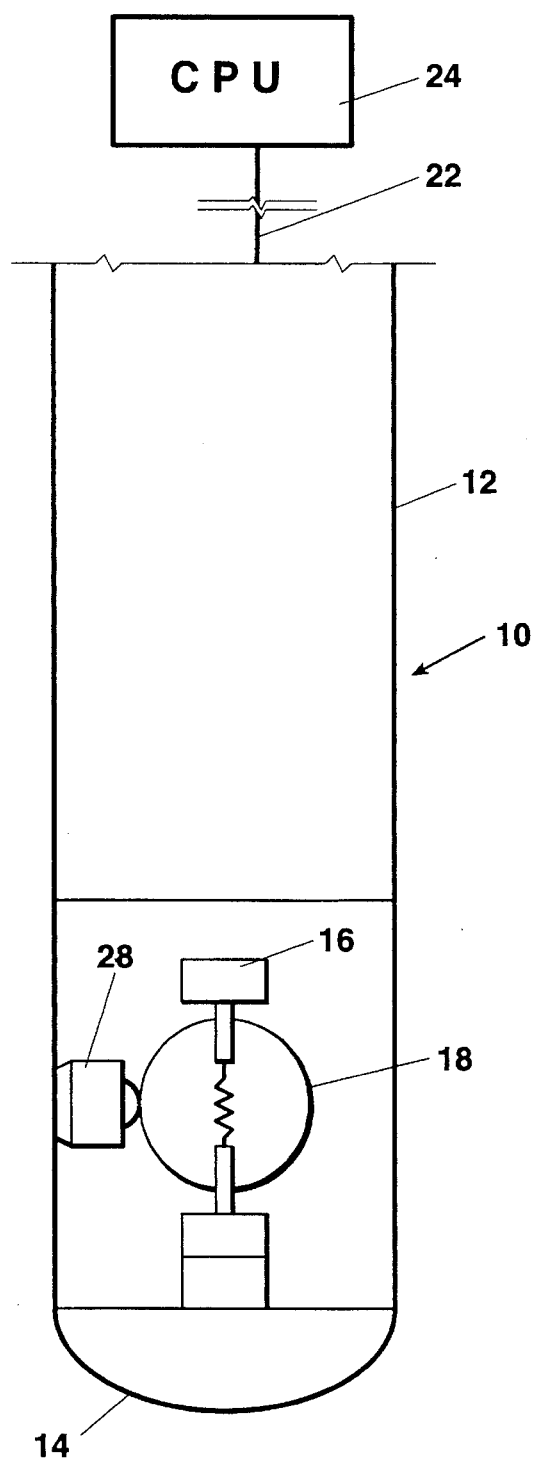
Fig. 2
Fig. 1

MOISTURE MONITOR APPARATUS FOR A FLUID SYSTEM

BACKGROUND OF THE INVENTION

1. Field of the Invention

The present invention is directed to a moisture monitor apparatus to determine and monitor the moisture and water content in a fluid.

2. Prior Art

Various types of fluids are used in industrial fluid systems. The condition of the fluid is determined not only by cleanliness but by other factors such as water content. Certain properties are known to effect the performance of fluids in the system such as viscosity, anti-wear properties, resistance to oxidation, resistance to rust, and freezing point properties.

Petroleum based oils are the widest used fluids in industrial fluid systems. Petroleum based oils have the ability to transmit fluid power efficiently and have good lubrication qualities. An important property of petroleum oil is resistance to chemical change. An accelerator of oxidation is the effect of contaminants, such as water. Additionally, rust may occur on machine surfaces in the fluid system because of the presence of water. Additionally, water in the system may freeze above the operating temperatures.

The source of water may be condensation from the air which is present in the fluid system. Water can also enter the fluid system through use of coolants during machinery operations.

The moisture or water content in the fluid system may be tested in a number of ways. In known crackle testing, a sample of oil is removed from the fluid system and is dipped onto a hot plate. As the fluid heats up, any moisture in the fluid begins to vaporize and a crackling/popping effect will be heard. This is due to the "miniature explosions" occurring at the water/oil boundary interface. The technician listens for a crackling sound made by the moisture in the oil. This type of testing does not quantify the amount of moisture in a fluid, only its presence and increases the possibility of sample contamination due to the dipping methods which may be applied.

Additionally, there are known laboratory methods of removing water from a fluid sample and quantifying the water.

There is a need, therefore, for a moisture monitor apparatus that will provide a quantitative moisture count.

There is also a need for a moisture monitor apparatus which may be used to take a sample and test for moisture, removing the possibility of sample contamination.

There is additionally a need for a moisture monitor apparatus that is lightweight and portable and may be used on-line with a fluid system in the field.

SUMMARY OF THE INVENTION

The present invention provides a moisture monitor apparatus to determine the level of moisture or water in a fluid system.

In one embodiment, the apparatus includes a probe having an end that may be submerged or placed in the fluid to be tested. A heater on the body is submerged in the fluid. A thin membrane on the body separates the heater from a microphone within the body. The microphone is, therefore, in a fluid-tight chamber within the body separated from the fluid.

When the heater is activated, the fluid surrounding the heater is heated. If there is any moisture in the fluid, the moisture begins to vaporize and an audible crackling/popping effect will be produced. The popping sound produces sound waves in the fluid. The thin membrane will allow sound waves to pass through the membrane. The membrane also will be caused to vibrate which acoustically enhances the sound waves in the air surrounding the microphone.

Through the use of the microphone, the sound waves are converted into electric voltage variations. The number of electric voltage surges over a certain minimum level is determined per unit of time. This number of surges per unit of time is then compared against a calibration curve with known moisture levels. It is, thus, possible to determine the level or parts per million of water or moisture in the fluid.

BRIEF DESCRIPTION OF THE DRAWINGS

FIG. 1 is a partial front view of one embodiment of a moisture monitor apparatus constructed in accordance with the present invention;

FIG. 2 is a partial side view of the moisture monitor apparatus shown in FIG. 1;

DETAILED DESCRIPTION OF THE PREFERRED EMBODIMENTS

Figure 5:
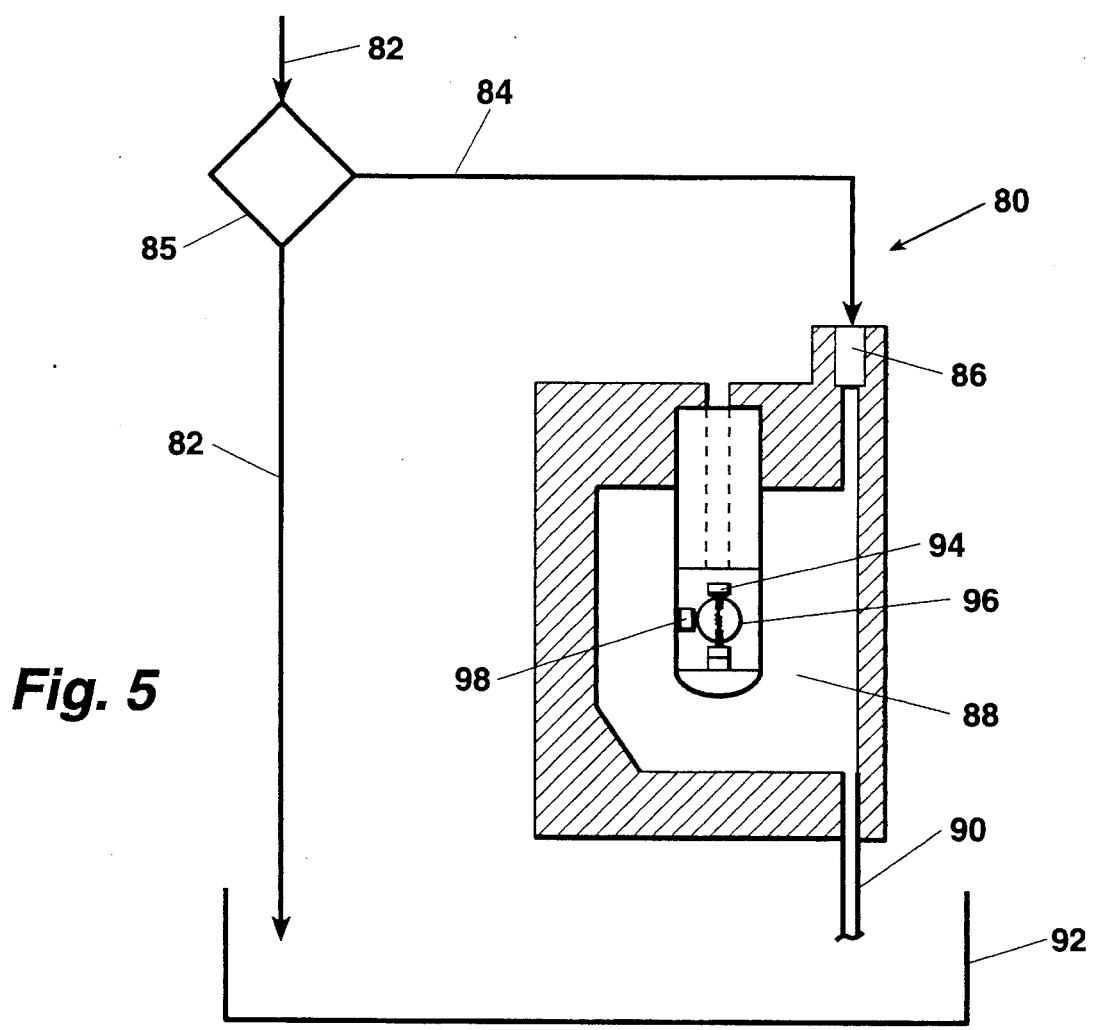
FIG. 5 is a simplified diagram of a further alternate embodiment of the moisture monitor apparatus of the present invention.

The present invention provides a moisture monitor apparatus to determine the level of moisture or water in a fluid system. As will be described herein, the invention may take a variety of configurations or embodiments.

Each embodiment takes advantage of the sound produced as moisture in the fluid begins to vaporize when heated. It is known that for a given unit of fluid, the acoustic energy releasable by a heating element depends on the percentage of water in the unit. Measurement of the acoustic energy is directly proportional to the water concentration in the sample.

FIGS. 1 and 2 show one configuration or embodiment of the moisture monitor apparatus constructed as a probe which may be placed into or dipped into a sample of the fluid or into the fluid system itself.

The apparatus 10 includes a probe body 12, a portion of which is shown in FIG. 1. The end 14 of the probe body 12 may be submersed in or placed in the fluid to be tested (not shown). One usage of the apparatus 10 is to take a reading from a sample container or bottle of the fluid. A heater in the form of a heating coil 16 extends from the surface of the body 12 and is submersed in the fluid. As the heating coil heats up, the fluid around the heating coil will be heated. While a heating coil is illustrated in the present embodiment, it will be recognized that other types of heaters might be employed.

A thin membrane 18 on the body 12 separates the heating coil from a condenser microphone 20 within the body. The microphone is, therefore, within a fluid tight chamber separated from the fluid. The membrane 18 may be fabricated from mylar or other thin material that will permit acoustics to be transmitted.

The microphone is connected by cables 22 which run through the body 12 and thereafter to a microprocessor 24 (illustrated by a block).

To use the apparatus 10, a switch (not shown) is activated to turn on the heating coil which is powered from a battery (not shown) or other power source. In one embodiment, the heating coil is powered by 3.3 volts of 6 amps.

The heating coil heats the fluid surrounding the heating coil. If there is any moisture in the fluid, the moisture will begin to vaporize and a crackling/popping effect will be produced. This is due to the sound of "miniature explosions" occurring at the water/oil boundary interface.

It is known that sound propogates as compressional waves in both liquid and gas. These crackling/popping sounds produce sound waves in the fluid which passes through the membrane. Additionally, the sound waves in the fluid cause the thin membrane 18 to vibrate in response, thus, acoustically enhancing the signal. The vibration of the membrane 18 causes sound waves in the air surrounding the microphone within the body 12.

The microphone, therefore, detects and receives the sounds produced from the heated fluid as the moisture vaporizes. Through the use of the condenser microphone, the sound waves are converted into electric voltage variations 30 as illustrated in the chart of FIG. 3.

Figure 3:
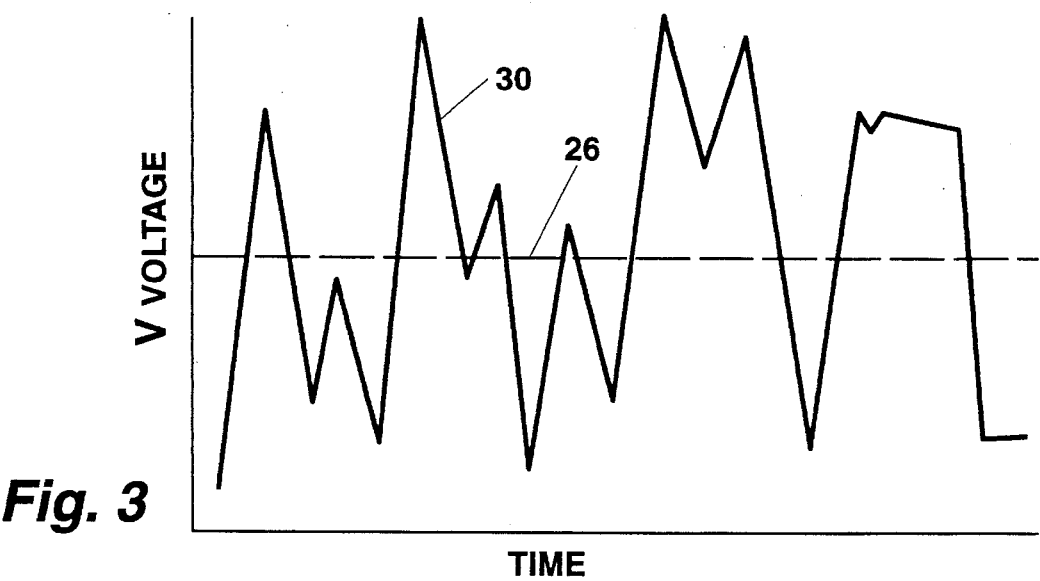
FIG. 3 is a chart showing voltage variations charted against time produced from a fluid sample using the moisture monitor apparatus of the present invention.

FIG. 3 illustrates a chart of a sample of fluid which has been analyzed with the present invention. The Y axis shows the voltage while the X axis shows time. The number of electric voltage surges over a minimum level, shown by dashed line 26 is determined per unit time. This number of surges per unit time is then compared against a calibration curve with known moisture levels. The calibration curve has previously been established from testing or has been entered into memory of the microprocessor from known data. It is, thus, possible to determine the level or parts per million of water or moisture in the fluid.

As seen in FIGS. 1 and 2, the apparatus 10 may include a feedback sensor 28. Juxtaposed in close relation to the heating coil 16, the feedback sensor in one embodiment is a photo diode which detects light emitted from the heater. In the event there is no fluid surrounding the heating coil, the coil will produce a bright light. If the photo diode detects light from the heater, a switch (not shown) will be activated to turn off the heating coil.

An optional initiation test might also be employed. The microphone will be used to determine the noise level in the test environment. If the environment is noisy, the user is notified and testing will stop.

Figure 4:
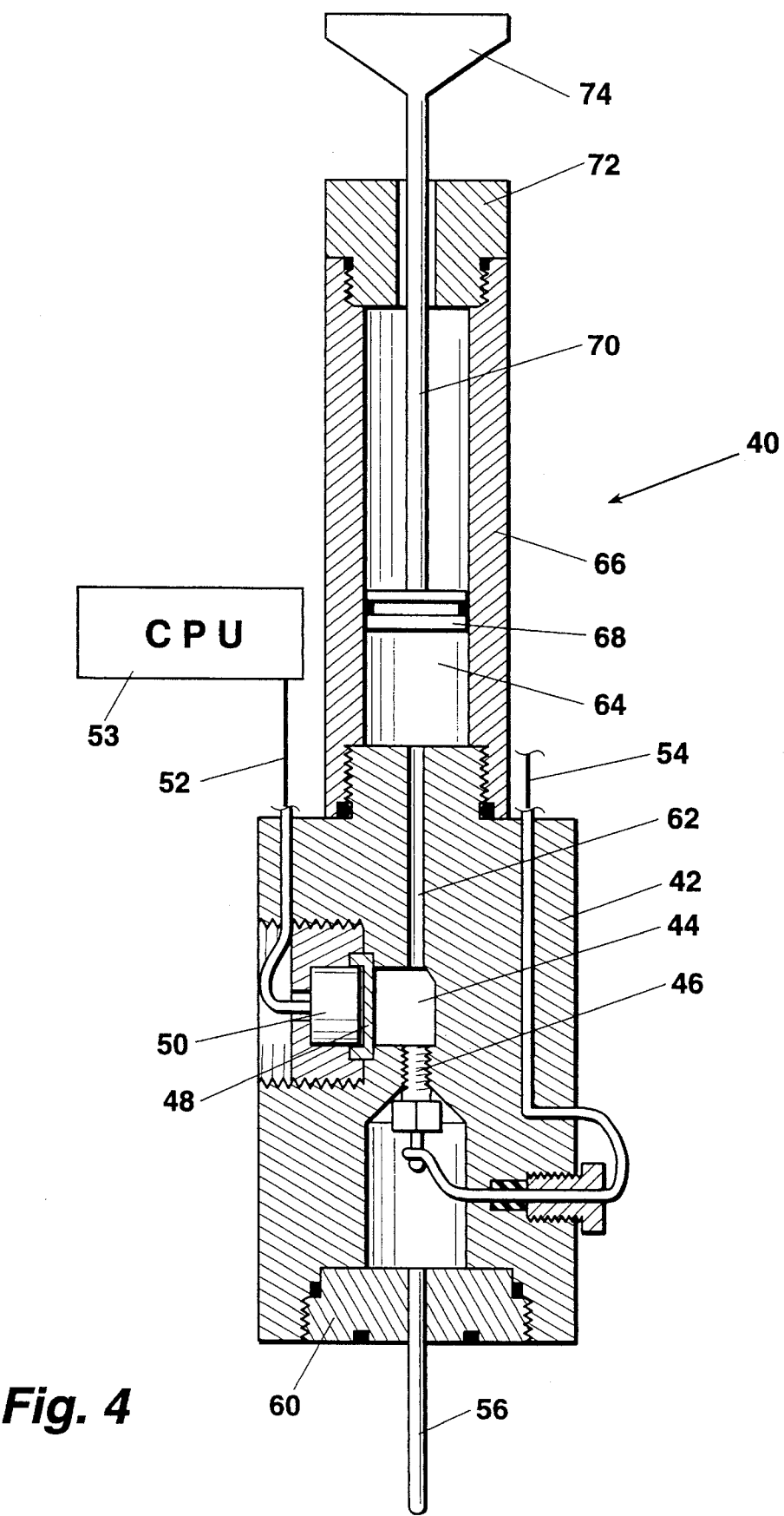
FIG. 4 is a sectional view of an alternate embodiment of the moisture monitor apparatus constructed in accordance with the present invention.

FIG. 4 illustrates a partial sectional view of an alternate embodiment 40 of the moisture monitor apparatus. The apparatus 40 includes a body 42 having a test chamber 44. A heater in the form of a heating plug 46 is in fluid communication with the test chamber 44. The fluid in the chamber is, thus, heated. It will be understood that other types of heaters may be employed within the chamber.

A thin membrane 48 separates the test chamber 44 from a microphone 50 within the body and thereafter to a microprocessor 53. Microphone power and signal wires 52 extend through the body. A power wire 54 extends through the body and connects to a power supply (not shown). The test chamber 44 is in fluid communication with an intake 56 extending from an end probe 60 which may be connected to the fluid system.

The test chamber 44 is also in fluid communication with a passage 62 which leads to a cavity 64 in a barrel 66. The barrel 66 has a reciprocating piston 68 connected to a rod 70 which extends through an end cap 72 of the barrel. The rod terminates outside the barrel in a handle 74.

When the apparatus 40 is connected to a fluid system, pressure from the fluid system will allow fluid to pass through the intake 56, into the test chamber 44, through the passage 62 and into the cavity 64. Fluid pressure will cause the piston to be displaced and the cavity to fill.

The fluid in the cavity may then be pushed back out of the cavity leaving fluid only in the test chamber 44. The fluid in the test chamber is thereafter heated by the heater 46. As the fluid heats up, the moisture in the water begins to vaporize and makes a crackling/popping sound. This is due to the sound of "miniature explosions" occurring at the water/oil boundary interface. The sound produces vibrations in the fluid that cause the membrane 48 to vibrate.

The vibrations cause sound waves in the air surrounding the microphone which are detected by the microphone 50. The sound is, thus, translated and converted into voltage variations. The voltage surge variations over a certain level are counted per unit time. The number of surges per unit time is then compared against a calibration curve with known moisture levels. The calibration may be done through various well-known techniques including using a moisture/water measuring instrument such as a Karl Fischer titrator. A number of oil samples are prepared with different levels of water content. The water levels are measured and then matched with the crackling sound counts. After repeating a sufficient number of tests, a calibration curve can be generated. This information is then stored in a microprocessor which may be used for the apparatus. This is analyzed through the use of a microprocessor leading directly to a quantitative moisture count.

FIG. 5 shows a further alternate embodiment of the apparatus 80. The embodiment of the apparatus 80 may be used on an inline basis with the fluid system. Fluid in the system is shown by arrows 82. A low pressure line 84 leads off of the fluid system line 82 through a valve 85. The low pressure line 84 leads to a solenoid valve 86 which may be opened to allow fluid to pass into an accumulating chamber 88. The chamber 88 has an exit 90 which may lead to a reservior 92 or a return. Within the accumulating chamber is a heating element such as a heating coil 94, a membrane 96 and a microphone (not visible in FIG. 5). A feedback sensor 98 may also be included. The low pressure line 84 and solenoid 86 will reduce the turbulence or fluid rate through the low pressure line.

When the heating coil 94 is activated, the fluid in the accumulating chamber is heated. If there is any moisture in the fluid, the moisture will begin to vaporize and an audible crackling/popping effect will be produced. These sounds produce sound waves in the fluid which causes the thin membrane to vibrate. Accordingly, a moisture determination may be made.

It will be understood that other types of inline embodiments are well within the scope of the invention. One type of inline apparatus 80 may be detachably connected to a fluid system through an existing fitting.

Whereas, the present invention has been described in relation to the drawings attached hereto, it should be understood that other and further modifications, apart from those shown or suggested herein, may be made within the spirit and scope of this invention.

What is claimed is:

1. A moisture monitor apparatus for a fluid system, which comprises:

heater means to heat a portion of fluid from said system in order to vaporize moisture therein;

microphone means adjacent and separated from a test chamber by a thin membrane to convert sounds from said test chamber into electric voltage variations; and means to translate said electric voltage variations into quantitative data including counting the number of surges above a certain voltage level per unit time and comparing the number to known calibration data.

2. A moisture monitor apparatus set forth in claim 1 including a detachable probe assembly to connect said test chamber with said fluid system.

3. A moisture monitor apparatus as set forth in claim 1 wherein said heater means includes an electric heater coil.

4. A moisture monitor apparatus as set forth in claim 1 wherein said means to translate said electric voltage variations into quantitative data includes a microprocessor.

5. A moisture monitor apparatus as set forth in claim 1 including a barrel cavity with a reciprocating piston therein, said barrel cavity in fluid communication with said test chamber.

6. A moisture monitor apparatus as set forth in claim 5 wherein said piston may be used to displace fluid from said barrel and through said test chamber.

7. A moisture monitor apparatus for a fluid system which apparatus comprises:

heater means in fluid communication with fluid in said system to heat and vaporize moisture in said fluid;

a microphone separated from said fluid by a thin membrane to convert sounds from said moisture being vaporized into electric voltage variations; and means to translate said electric voltage variations into quantitative data including counting the number of voltage surges above a certain voltage per unit time and comparing the number to known calibration data.

8. A moisture monitor apparatus as set forth in claim 7 wherein said heater means and said microphone are mounted on a body.

9. A process to monitor moisture in a fluid system, which process comprises:

filling a test chamber with a portion of fluid from said fluid system;

heating said fluid in said test chamber to vaporize moisture therein;

transmitting sounds from said test chamber and converting them into electric voltage variations through a microphone separated from said fluid by a thin membrane; and translating said electric voltage variations into quantitative data by counting the number of voltage surges above a certain voltage level per unit time and comparing against a calibration curve.

10. A method of detecting the quantity of water in a fluid mixture comprising:

(a) heating said mixture in-line with a fluid system to the boiling point of water to cause any water contained in said mixture to vaporize;

(b) detecting sound generated as acoustic emissions as water in said mixture passes from a liquid to a vapor phase;

(c) converting said sound detected in step (b) to electrical signals; and (d) translating said electrical signals of step (c) into quantitative data.

11. A moisture monitor apparatus as set forth in claim 1 wherein said test chamber is within said apparatus to hold said portion of fluid from said system for said heating.

12. A moisture monitor apparatus as set forth in claim 7 wherein a test chamber within said apparatus is in fluid communication with said heater means.

* * * * *